United States Patent
Fukuda et al.

(10) Patent No.: US 7,032,600 B2
(45) Date of Patent: Apr. 25, 2006

(54) METHOD AND SYSTEM FOR MEASURING A POSITION, POSITION MEASURING DEVICE, AND AN IN VIVO RADIO DEVICE

(75) Inventors: Atsushi Fukuda, Yokohama (JP); Yoshiaki Tarusawa, Yokosuka (JP); Noriyoshi Terada, Yokosuka (JP)

(73) Assignee: NTT DoCoMo, Inc., Tokyo (JP)

( * ) Notice: Subject to any disclaimer, the term of this patent is extended or adjusted under 35 U.S.C. 154(b) by 0 days.

(21) Appl. No.: 10/758,232

(22) Filed: Jan. 16, 2004

(65) Prior Publication Data

US 2004/0210131 A1  Oct. 21, 2004

(30) Foreign Application Priority Data

Jan. 16, 2003  (JP) .............................. 2003-008739

(51) Int. Cl.
*A61B 19/00* (2006.01)
(52) U.S. Cl. ...................................... 128/899
(58) Field of Classification Search ........ 128/897–899; 600/407, 117, 424; 702/152, 150
See application file for complete search history.

(56) References Cited

U.S. PATENT DOCUMENTS

| | | |
|---|---|---|
| 4,799,062 A | 1/1989 | Sanderford, Jr. et al. |
| 5,395,366 A | 3/1995 | D'Andrea et al. |
| 6,334,073 B1 | 12/2001 | Levine |

FOREIGN PATENT DOCUMENTS

| | | |
|---|---|---|
| EP | 0 646 313 | 4/1995 |
| EP | 0 667 115 | 8/1995 |
| JP | 2001-46357 | 2/2001 |
| WO | WO 02/076193 | 10/2002 |

OTHER PUBLICATIONS http://www..rfnorika.com/e_system/e_system_001.html, 9 pages, "Endoscopic Capsule, Norika", Mar. 3, 2004.

*Primary Examiner*—John P. Lacyk
(74) *Attorney, Agent, or Firm*—Oblon, Spivak, McClelland, Maier & Neustadt, P.C.

(57) ABSTRACT

A system for measuring the position of an in vivo radio device is disclosed. The system comprises the in vivo radio device administered into a living organism, a plurality of ex vivo radio devices disposed outside of the living organism, and a position measuring device. The in vivo radio device includes a transmitter for transmitting a vital information signal or a position measuring signal. Each of the ex vivo radio devices includes a receiver for receiving the vital information signal or the position measuring signal. The position measuring device includes a position measuring unit for measuring the position of the in vivo radio device based on receiving characteristics of the vital information signal or the position measuring signal received by the ex vivo radio devices.

8 Claims, 9 Drawing Sheets

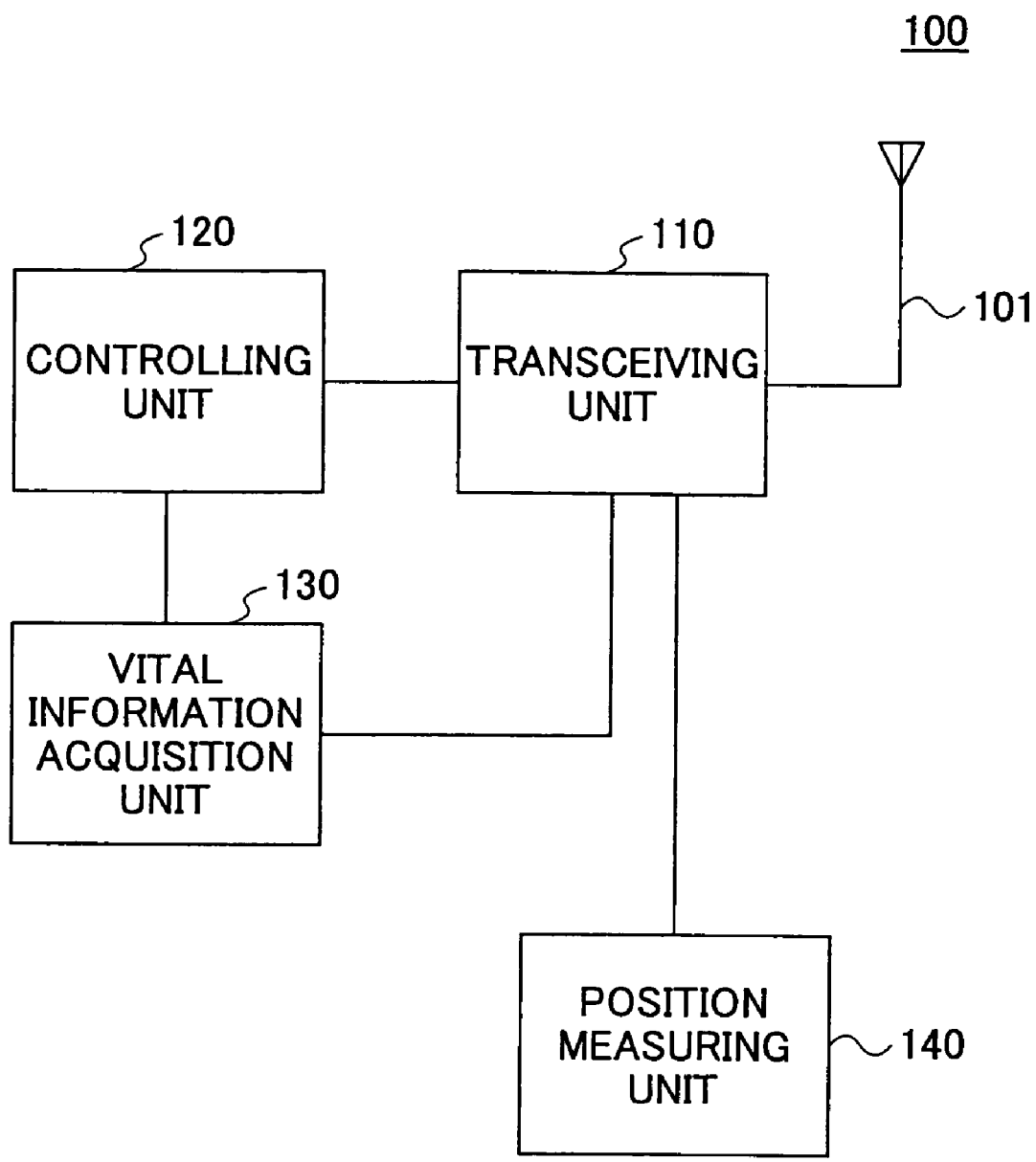

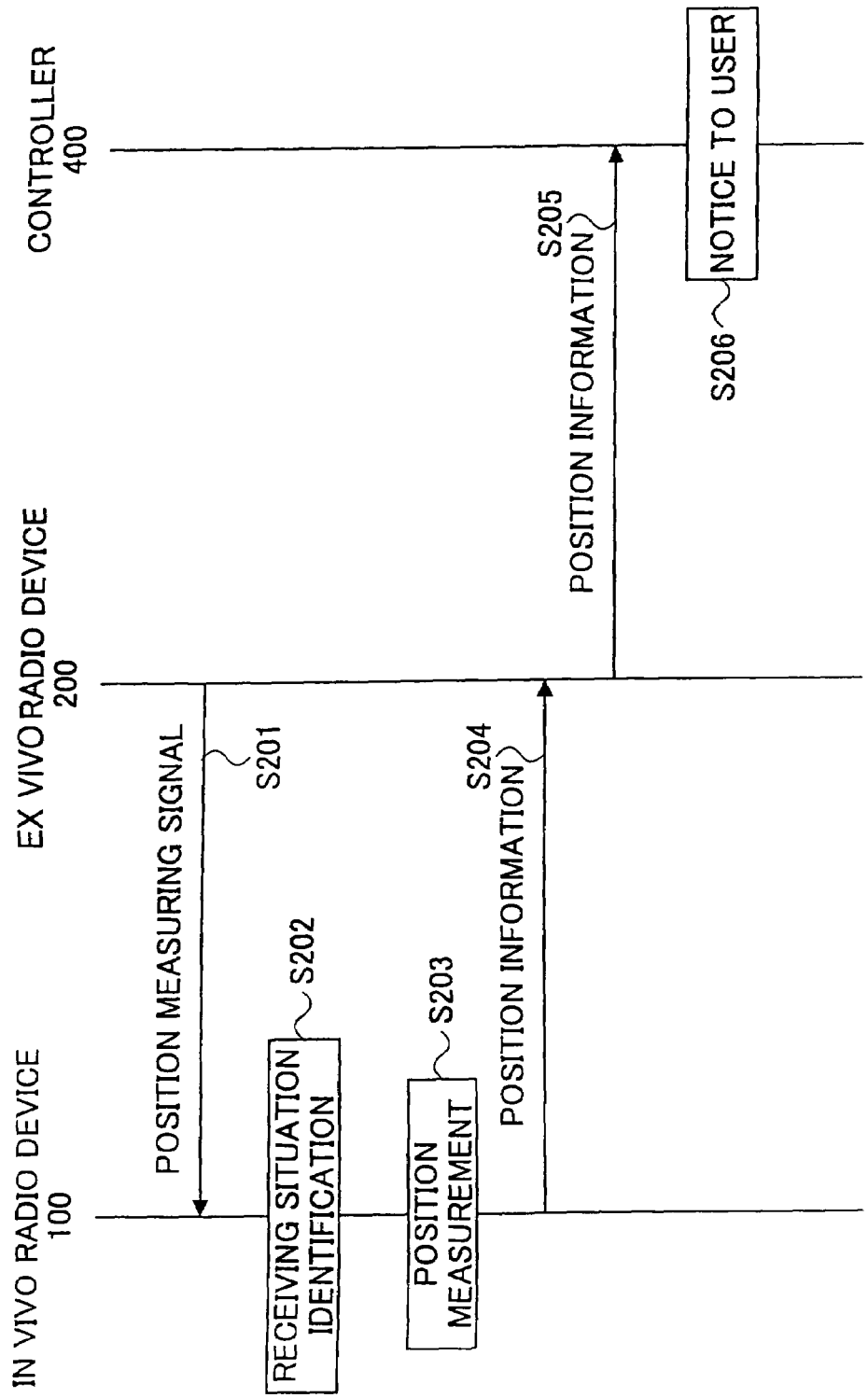

METHOD AND SYSTEM FOR MEASURING A POSITION, POSITION MEASURING DEVICE, AND AN IN VIVO RADIO DEVICE

BACKGROUND OF THE INVENTION

1. Field of the Invention

The present invention generally relates to methods and systems for measuring the position of an in vivo radio device, such position measuring devices, and in vivo radio devices, and specifically relates to such a method and system for measuring the position of the in vivo radio device based on receiving characteristics of position measuring signals.

2. Description of the Related Art

Endoscopes have long been used as medical devices for acquiring in vivo information and taking it to the outside. The endoscope is a camera mounted at an end of a cable. The camera takes pictures of a selected place (e.g., a diseased part) in a human body, and transmits the pictures via the cable to display them on a monitor device outside of the human body. However, the camera has to be swallowed and the cable has to be moved around in the human body to carry the camera to the selected place, and therefore a great burden is imposed on the patient.

In order to mitigate the burden on the patient, it was envisaged that electromagnetic waves can be used for transmitting vital information acquired in the human body to the outside. In this scheme, a patient swallows a small-sized capsule endoscope with a built-in camera. This ingested capsule endoscope moves in the patient's body and takes pictures of the gastrointestinal tract in response to control signals transmitted from outside of the patient's body. The pictures taken are transmitted from the capsule to a monitor device outside of the patient's body by RF, and displayed on the monitor device. One good example of such capsules is published on the Internet Website at www.rfnorika.com with a title "Endoscope Capsule NORIKA System".

When doctors use such pictures or images displayed on the monitor to diagnose, it is essential for them to know precisely where in the patient's body the images were taken or where the administered capsule is located in the patient's body at present.

SUMMARY OF THE INVENTION

Accordingly, it is one object of the present invention to provide a method, system and device for precisely measuring the position of a device administered in a living organism, such position measuring devices, and in vivo radio devices; and more specifically that relates to such a method and system for measuring the position of the in vivo radio device based on receiving characteristics of (the information contained in) position measuring signals.

Another and more specific object of the present invention is to provide a method for measuring the position of an in vivo radio device administered into a living organism, comprising the steps of transmitting a vital information signal or a position measuring signal by the in vivo radio device; receiving the vital information signal or the position measuring signal by a plurality of ex vivo radio devices disposed outside of the living organism; and measuring the position of the in vivo radio device, based on receiving characteristics of the vital information signal or the position measuring signal received by the ex vivo radio devices.

According to another feature of the present invention, there is provided a position measuring system comprising an in vivo radio device administered into a living organism, a plurality of ex vivo radio devices disposed outside of the living organism, and a position measuring device, wherein, the in viva radio device includes a transmitter for transmitting a vital information signal or a position measuring signal; each of the ex vivo radio devices includes a receiver for receiving the vital information signal or the position measuring signal; and the position measuring device includes a position measuring unit for measuring the position of the in vivo radio device based on receiving characteristics of the vital information signal or the position measuring signal received by the ex vivo radio devices.

According to further feature of the present invention, there is provided a position measuring system comprising an in vivo radio device administered into a living organism, and a plurality of ex vivo radio devices disposed outside of the living organism, wherein, each of the ex vivo radio devices includes a transmitter for transmitting a position measuring signal; and the in vivo radio device includes a receiver for receiving the position measuring signals from the ex vivo radio devices, and a position measuring unit for measuring the position of the in vivo radio device based on receiving characteristics of the position measuring signals from the ex vivo radio devices.

According to another feature of the present invention, there is provided a position measuring device for measuring the position of an in vivo radio device administered into a living organism, comprising: a position measuring unit for measuring the position of the in vivo radio device, based on receiving characteristics of a vital information signal or a position measuring signal transmitted from the in vivo radio device and received by a plurality of ex vivo radio devices.

In the above position measuring device, the position measuring unit may measure the position of the in vivo radio device, based on differences in receiving times of the vital information signals or the position measuring signals received by the ex vivo radio devices, phase differences of the vital information signals or the position measuring signals received by the ex vivo radio devices, or arriving directions of the vital information signals or the position measuring signals received by the ex vivo radio devices.

According to another feature of the present invention, there is provided an in vivo radio device to be administered into a living organism, comprising; a receiver for receiving position measuring signals transmitted from a plurality of ex vivo radio devices; and a position measuring unit for measuring the position of the in vivo radio device, based on receiving characteristics of the position measuring signals received from the ex vivo radio devices.

In the above in vivo radio device, the position measuring unit may measure the position of the in vivo radio device, based on differences in receiving times of the position measuring signals received from the ex vivo radio devices, phase differences of the position measuring signals received from the ex vivo radio devices, or arriving directions of the position measuring signals transmitted by the ex vivo radio devices and received by the in vivo radio device.

The position measuring unit may notify the ex vivo radio devices of the measured position.

Features and advantages of the present invention are set forth in the description that follows, and in part will become apparent from the description and the accompanying drawings, or may be learned by practice of the invention according to the teachings provided in the description. Objects as well as other features and advantages of the present invention will be realized and attained by a method, system and device particularly pointed out in the specification in such full, clear, concise, and exact terms as to enable a person having ordinary skill in the art to practice the invention.

BRIEF DESCRIPTION OF THE DRAWINGS

FIG. 10 is a block diagram of an in vivo radio device according to the second embodiment of the present invention; and FIG. 11 is a sequence chart illustrating operation of the position measuring system according the second embodiment of the present invention.

DESCRIPTION OF THE PREFERRED EMBODIMENTS

In the following, embodiments of the present invention are described with reference to the accompanying drawings.

Embodiment 1

Figure 1:
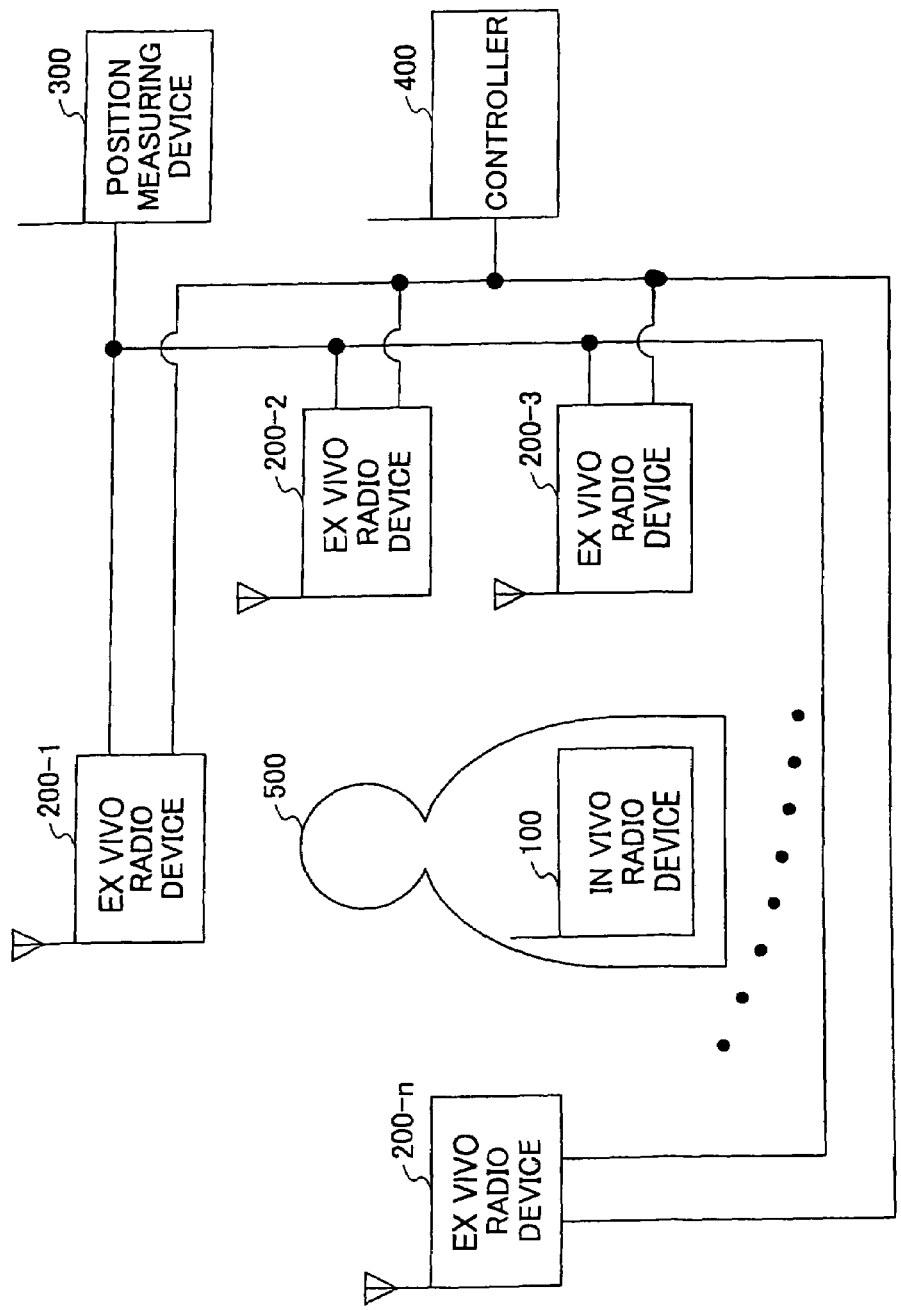
FIG. 1 is a block diagram of a position measuring system according to a first embodiment of the present invention.

FIG. 1 shows a schematic block diagram of a position measuring system according to a first embodiment (Embodiment 1) of the present invention. The position measuring system includes an in vivo radio device 100 administered into a human body, ex vivo radio devices 200-1, 200-2, . . . 200-*n* disposed outside of the human body (herein after collectively referred to as "ex vivo radio devices 200"), a position measuring device 300 and a controller 400.

In the position measuring system according to the first embodiment, each of the ex vivo radio devices 200 receives a signal transmitted from the in vivo radio device 100, The position measuring device 300 measures or determines the position of the in vivo radio device 100 based on receiving characteristics of the received signals.

Figure 2:
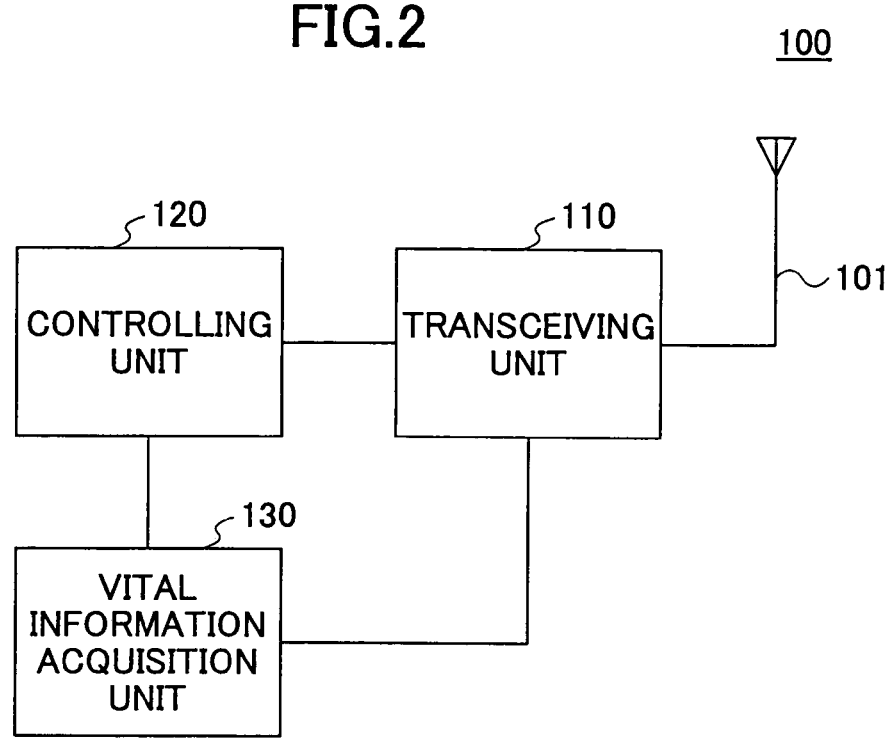
FIG. 2 is a block diagram of an in vivo radio device according to the first embodiment of the present invention.

FIG. 2 is a schematic block diagram of the in vivo radio device 100 in the first embodiment. The in vivo radio device 100 includes an antenna 101, a transceiving unit 110, a controlling unit 120 and a vital information acquisition unit 130.

A control signal transmitted by the controller 400 through the ex vivo radio devices 200 is received by the transceiving unit 110 through the antenna 101. The thus received control signal is supplied to the controlling unit 120 to control the operation of the in vivo radio device 100. Based on the control signal, the controlling unit 120 controls the movement of the in vivo radio device 100, provides medication, or conducts in vivo ablation. The controlling unit 120 further controls the vital information acquisition unit 130 based on the received control signal. The vital information acquisition unit 130 includes a built-in camera and a built-in microphone, and takes pictures and collects sounds within the human body and transmits the acquired vital information such as an image signal and a sound signal to the transceiving unit 110.

Figure 3:
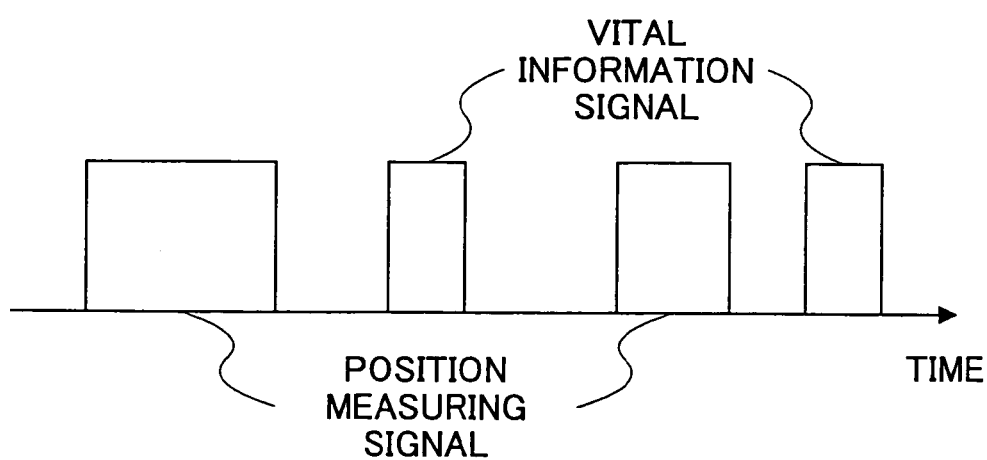
FIG. 3 is a timing chart showing multiplexing of vital information signals and position measuring signals.

The transceiving unit 110 transmits the vital information through the antenna 101 to outside of the human body. Alternatively, the transceiving unit 110 regularly transmits a position measuring signal in addition to the vital information through the antenna 101 to outside of the human body. When the transceiving unit 110 transmits both the vital information signal and the position measuring signal, these signals are multiplexed as shown in FIG. 3.

Each of the ex vivo radio devices 200 receives the vital information signal and position measuring signal, and transmits those signals to the position measuring device 300. The position measuring device 300 measures the position of the in vivo radio device 100 based on the receiving characteristics of the vital information signal and position measuring signal.

Figure 4:
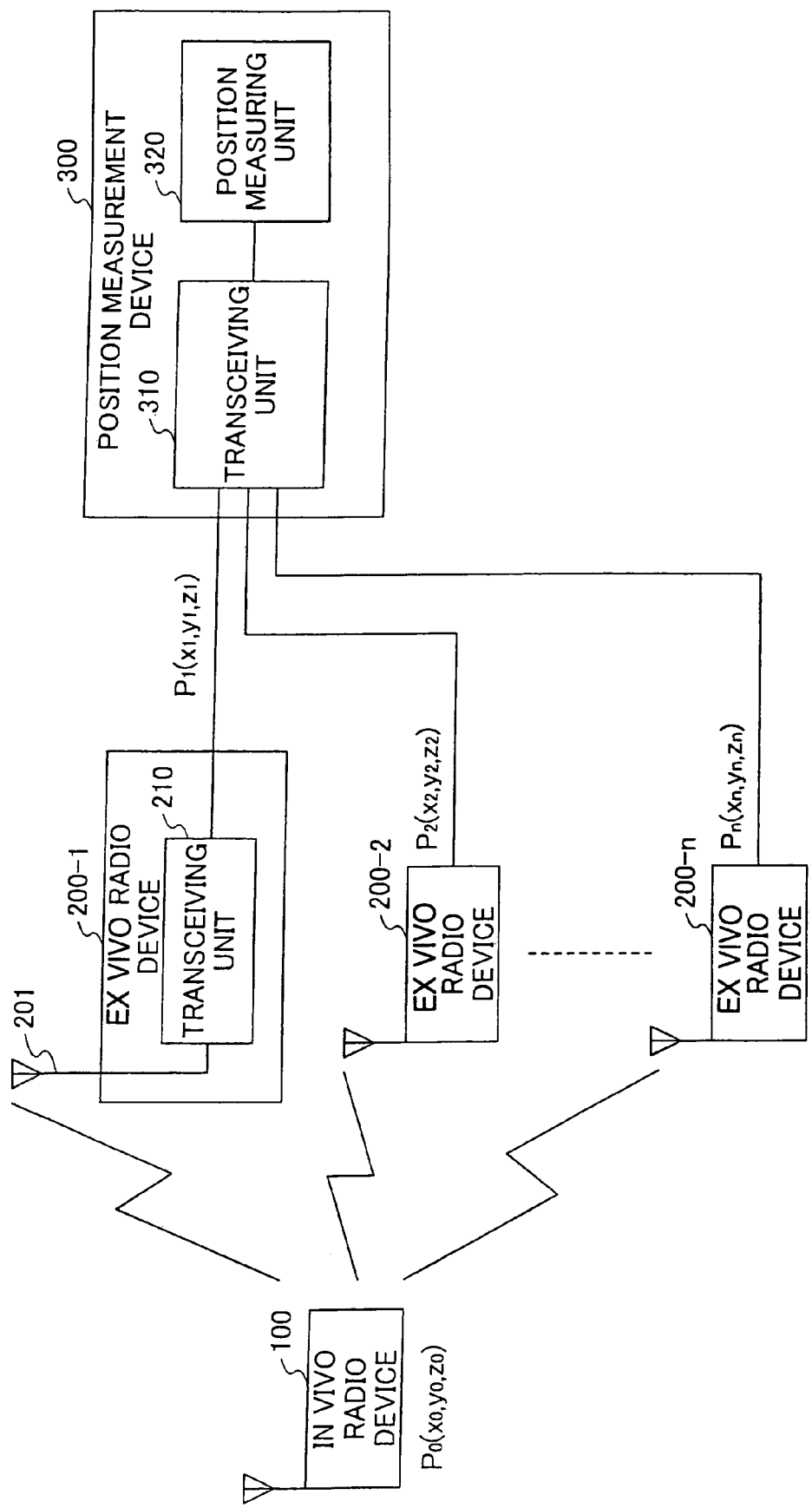
FIG. 4 is a block diagram of an ex vivo radio device and a position measuring device according to the first embodiment of the present invention.

FIG. 4 is a schematic block diagram of the ex vivo radio devices 200 and the position measurement device 300 in the first embodiment. Each of the ex vivo radio devices 200 includes a transceiving unit 210. A structure of only the ex vivo radio device 200-1 is shown in FIG. 4, but other ex vivo radio devices 200-2, . . . 200-*n* have the same structure. On the other hand, the position measurement device 300 includes a transceiving unit 310 and a position measuring unit 320.

Embodiments 1-1, 1-2 and 1-3 are explained below. In the embodiment 1-1, the position measuring unit 320 measures the position of the in vivo radio device 100 based on differences in times when the ex vivo radio devices 200 receive the signal. In the embodiment 1-2, the position measuring unit 320 in the position measurement device 300 measures the position of the in vivo radio device 100 based on phase differences in signals received by the ex vivo radio devices 200. In the embodiment 1-3, the position measuring unit 320 measures the position of the in vivo radio device 100 based on arriving directions of signals received by the ex vivo radio devices 200.

Embodiment 1-1

In this embodiment, the position measurement device 300 measures the position of the in vivo radio device 100 based on differences in times when the ex vivo radio devices 200 receive the signal. More specifically, when the transceiving unit 110 in the in vivo radio device 100 transmits the vital information signal or the position measuring signal, it also transmits information on the time of transmitting (hereinafter referred to "transmission time") as a part of the vital information signal or the position measuring signal. When the transceiving unit 210 in each of the ex vivo radio devices 200 receives the vital information signal or the position measuring signal and transmits them to the position measurement device 300, it also sends information on the time of receiving those signals (hereinafter referred to "reception time") as a part of the vital information signal or the position measuring signal to the position measurement device 300. The transceiving unit 310 in the position measurement device 300 receives the vital information signal or the position measuring signal transmitted from each of the ex vivo radio devices 200 and transmits them to the position measuring unit 320.

The position measuring unit 320 measures or determines the position of the in vivo radio device 100 based on the transmission time and the reception time included in the vital information signal or the position measuring signal. More specifically, the position measuring unit 320 in the position measurement device 300 generates the following Equation 1 for a distance $r_i$ between the in vivo radio device 100 and the ith ex vivo radio device 200-$i$, based on the transmission time $t_0$, the corresponding reception time $t_i$, and the light speed c.

Equation 1:

$$r_i = c(|t_0 - t_i|)$$

Since materials in the human body 500 are dielectric, the light speed c here is different from that in the vacuum of space. Therefore it is desirable to use a corrected light speed considering the permittivity of materials on the route from the in vivo radio device 100.

The position measuring unit 320 generates the following Equation 2 for the distance $r_i$ between the in viva radio device 100 and the ith ex vivo radio device 200-$i$, based on the position $(x_0, y_0, z_0)$ of the in vivo radio device 100 and the position $(x_i, y_i, z_i)$ of the ith ex vivo radio device 200-$i$.

Equation 2:

$$r_i = \sqrt{(x_0-x_i)^2 + (y_0-y_i)^2 + (z_0-z_i)^2} + S$$

Herein s means an influence given by time difference among the ex viva radio devices 200.

The position measuring unit 320 generates Equations 1 and 2 above regarding the distances between the in vivo radio device 100 and four ex vivo radio devices 200, and obtains four unknown values $x_0$, $y_0$, $z_0$, and s. If there is no time difference among the ex vivo radio devices 200, then s=0. In this case, the position measuring unit 320 generates Equations 1 and 2 above regarding the distances between the in vivo radio device 100 and three ex vivo radio devices 200, and obtains three unknown values $x_0$, $y_0$, and $z_0$.

Embodiment 1-2

In this embodiment, the position measurement device 300 measures the position of the in vivo radio device 100 based on phase differences in signals received by the ex vivo radio devices 200. More specifically, the position measuring unit 320 in the position measurement device 300 generates the following Equation 3 representing a receiving phase $\phi_i$ of the vital information signal or the position measuring signal received by the ith ex vivo radio device 200-$i$, based on a wavelength $\lambda$ of the vital information signal or the position measuring signal, a position $p_0$ of the in vivo radio device 100, and a position $p_i$ of the ith ex vivo radio device 200-$i$.

Equation 3:

$$\phi_i = \frac{2\pi}{\lambda}(\|p_0 - p_i\| - k_i\lambda)$$

Herein $k_i$ means a predetermined value corresponding to the ith ex vivo radio device 200-$i$.

The position measuring unit 320 obtains the received vital information signal or the position measuring signal by the following Equation 4:

$$r_i(t) = \exp[j\phi_i]$$

Then the position measuring unit 320 calculates a phase difference $\Delta\phi_{ij} \equiv \phi_i - \phi_j$ between a phase $\phi_i$ of the signal received by the ith ex vivo radio device 200-$i$ and a phase $\phi_j$ of the signal received by the jth ex vivo radio device 200-$j$, by obtaining correlation between these signals with using the following Equation 5:

$$\mathrm{Arg}\langle r_i'(t) r_j'^*(t)\rangle = \exp[j(\phi_i - \phi_j)] = \exp[j\phi_{ij}]$$

Herein < > means time average, and * means complex conjugate.

On the other hand, a distance difference $r_{ij}$ between the distance $r_i$ between the in vivo radio device 100 and the ith ex vivo radio device 200-$i$ and the distance $r_j$ between the in vivo radio device 100 and the jth ex vivo radio device 200-$j$ can be represented by the following Equation 6 using a position $(x_0, y_0, z_0)$ of the in vivo radio device 100, a position $(x_i, y_i, z_i)$ of the ith ex vivo radio device 200-$i$, and a position $(x_j, y_j, z_j)$ of the jth ex vivo radio device 200-$j$.

Equation 6

$$r_{ij} = \sqrt{(x_0-x_i)^2 + (y_0-y_i)^2 + (z_0-z_i)^2} - \sqrt{(x_0-x_j)^2 + (y_0-y_j)^2 + (z_0-z_j)^2}$$

The position measuring unit 320 obtains this distance difference $r_{ij}$, based on the phase $\Delta\phi_{ij}$ using the following Equation 7:

$$r_{ij} = 2\pi/\lambda(\Delta\phi_{ij} + 2\pi N_{ij})$$

Herein $N_{ij}$ means an integer bias of signal route difference and a known or presumable value.

The position measuring unit 320 forms three groups, each of which consists of two ex vivo radio devices 200, and substitutes the phase differences corresponding to each group in Equation 7 to obtain each $r_{ij}$. Then the position measuring unit 320 substitutes each of the obtained values $r_{ij}$ in Equation 6 to form three simultaneous equations. Then the position measuring unit 320 obtains the position $(x_0, y_0, z_0)$ of the in vivo radio device 100 by solving the three simultaneous equations.

Figure 5:
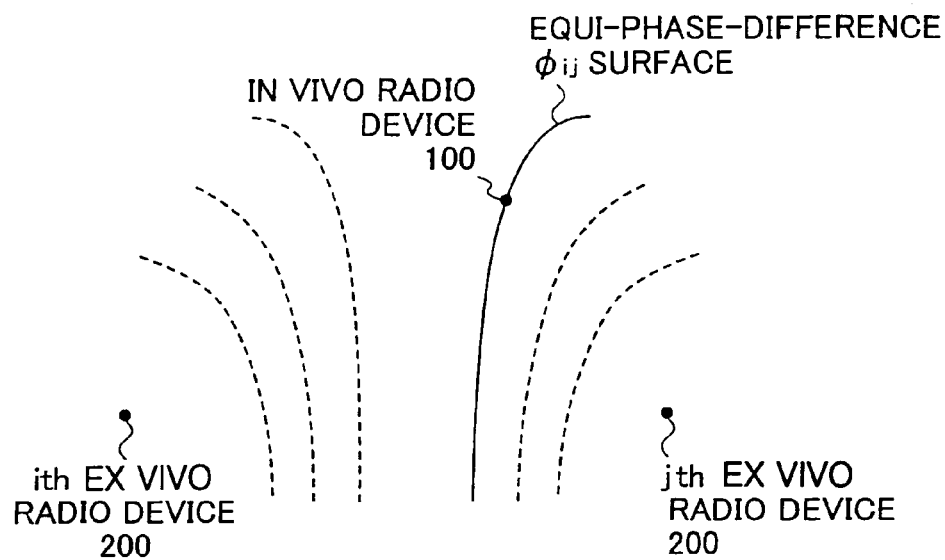
FIG. 5 is a graph illustrating an example of equi-phase-difference surfaces.

The position $(x_0, y_0, z_0)$ of the in vivo radio device 100 satisfying Equation 6 lies on a first equi-phase-difference surface (paraboloid) of a first phase difference $\Delta\phi_{ij}$ corresponding to two ex vivo radio devices 200-$i$, 200-$j$, as shown in FIG. 5. The intersection point of the first equi-phase-difference surface and another equi-phase-difference surface corresponding to another group of another two ex vivo radio devices should be the position of the in vivo radio device 100.

Embodiment 1-3

Figure 6:
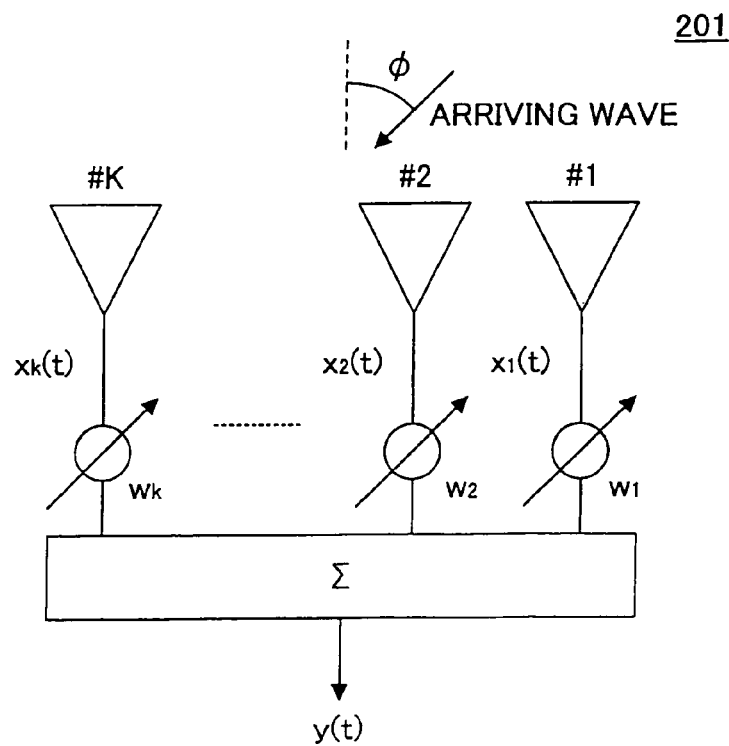
FIG. 6 schematically illustrates a linear array antenna system.

In this embodiment, the position measurement device 300 measures the position of the in vivo radio device 100 based on arriving directions of signals received by the ex vivo radio devices 200. In this case, the antenna 201 in each of the ex vivo radio devices 200 is an array antenna, especially a linear array antenna for a simple structure. FIG. 6 shows a schematic view of a linear array antenna including K elements.

An output (an array output) y(t) of the linear array antenna shown in FIG. 6 can be represented by the following Equation 8:

$$y(t) = W^H X(t)$$

Herein the input vector X(t) is represented by the following Equation 9:

$$X(t)=[x_1(t), x_2(t), \ldots, x_k(t)]^T$$

and W is represented by the following Equation 10:

$$W=[w_1, w_2, \ldots, w_k]^T$$

The position measuring unit 320 in the measurement device 300 calculates the output power $P_{out}$ by the following Equation 11, based on the array output y(t).

Equation 11:

$$P_{out} = \frac{1}{2}E[|y(t)|^2] = \frac{1}{2}W^H R_{xx} W$$

Herein $R_{xx}$ is represented by the following Equation 12:

$$R_{xx}=E[X(t)X^H(t)]$$

Then, the position measuring unit 320 calculates directional vectors V of the signals arriving at the antennas 201 of the ex vivo radio devices 200, by using the following Equation 13:

$$V = \left[\exp\left(-j\frac{2\pi}{\lambda}d_1\sin\phi\right), \ldots, \exp\left(-j\frac{2\pi}{\lambda}d_k\sin\phi\right)\right]^T \equiv a(\phi)$$

Herein $\phi$ means an arriving angle, and $d_k$ means a distance between a predetermined reference point and the kth element of the antenna 201. The input vector X(t) is represented by the following Equation 14:

$$X(t)=F(t)a(\phi)+N(t)$$

Herein F(t) is a wave form of the signal arriving at the antenna 201. N(t) means a thermal noise vector, whose components show zero dispersion and $\sigma_2$ independent complex gauss transition. The position measuring unit 320 drives the antenna 201 and changes its directional angle $\phi$ from minus 90 degrees to plus 90 degrees, to ascertain the peak output power $P_{out}$ of the linear array antenna. The position measuring unit 320 calculates the output power Pout of the linear array antenna by the following Equation 15 wherein the peak arriving angle is represented by $\phi$.

Equation 15:

$$P_{out} = \frac{1}{2}a^H(\phi)R_{xx}a(\phi)$$

The position measuring unit 320 further normalizes this output power $P_{out}$ of the linear array and calculates angle distribution of the arriving signals by the following Equation 16:

$$P_{BF}(\phi) = \frac{P_{out}}{a^H(\phi)a(\phi)/2} = \frac{a^H(\phi)R_{xx}a(\phi)}{a^H(\phi)a(\phi)}$$

The position measuring unit 320 identifies an arriving direction by the peak of $P_{BF}(\phi)$ obtained by Equation 16. The position measuring unit 320 further identifies at least three arriving directions at antennas 201 in at least three ex vivo radio devices 200. Then the position measuring unit 320 identifies the intersection point of the directional vectors indicating the corresponding arriving directions, as the position of the in vivo radio device 100.

If a moving route of the in viva radio device 100 is known, the position measuring unit 320 can improve the accuracy of the position of the in vivo radio device by utilizing the route information.

Figure 7:
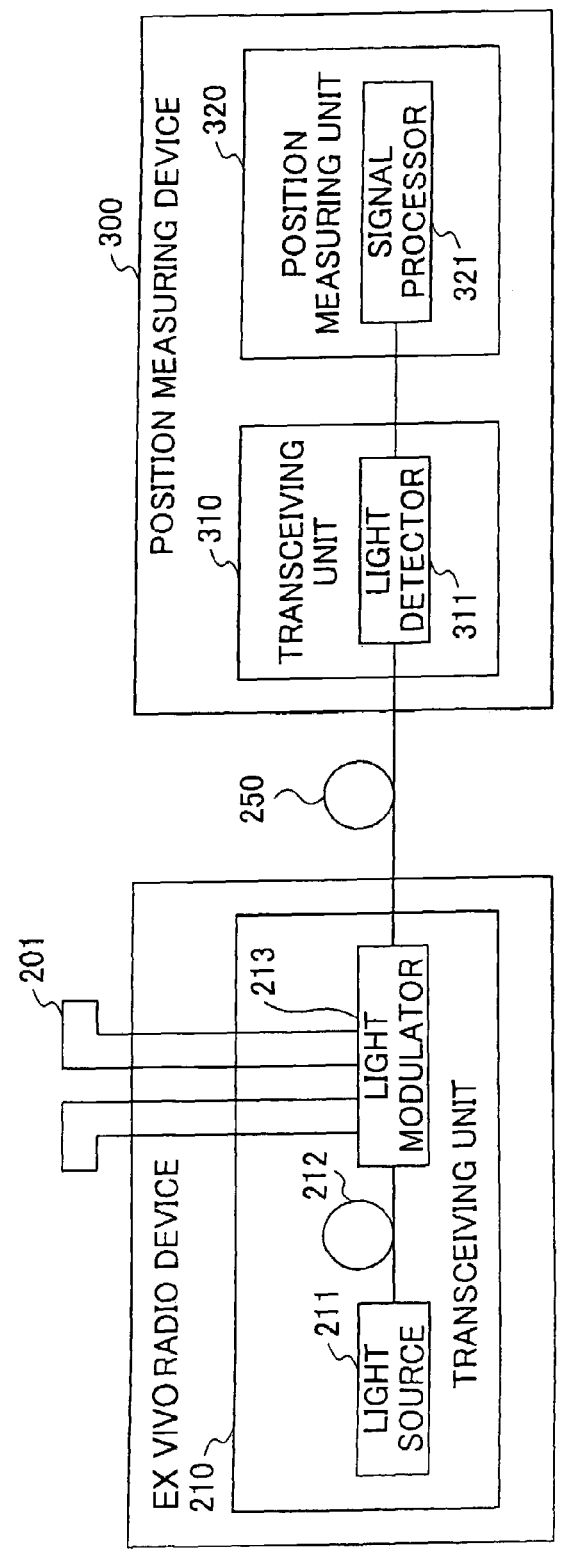
FIG. 7 is a block diagram of an ex vivo radio device and a position measuring device employing optical communication technology according to the first embodiment of the present invention.

In order to increase the accuracy of the position measurement, the ex vivo radio devices 200 have to avoid interference by others and transmit signals efficiently as much as possible. FIG. 7 is a block diagram of an exemplified ex vivo radio device 200 and position measuring device 300 that have adopted optical technology to transmit signals efficiently.

An antenna 201 and a transceiving unit 210 of the ex vivo radio device 200 form a light modulation optical sensor. The antenna 201 comprises two metal electrode bars disposed serially with a gap in an electromagnetic field. A light modulator 213 in the transceiving unit 210 converts an electric voltage induced within the gap to an optical signal. The converted optical signal is transmitted via an optical fiber 250 to the position measuring device 300. A light source 211 is provided in the transceiving unit 210. The light source 211 may be a high power semiconductor excited YAG laser and supplies light via an optical fiber 212 to the light modulator 213. The light modulator 213 may be a highly sensitive Mach-Zender light interferometer and can improve the sensitivity of the converted light signal by the light supplied from the light source 211.

A transceiving unit 310 in the position measuring device 300 includes a light detector 311. The light detector 311 converts the light signal transmitted by the light modulator 213 in the ex vivo radio device 200 to an electric signal. The position measuring unit 320 is equipped with a signal processor 321. The signal processor 321, based on the electric signal transmitted from the light detector 311, performs signal processing to measure the position of the in vivo radio device 100 by the above mentioned techniques.

In this manner, converting a signal from the in vivo radio device to a light signal and transmitting the light signal to the position measuring device 300 can avoid interference during transmission and improve the accuracy of position measurement.

Figure 8:
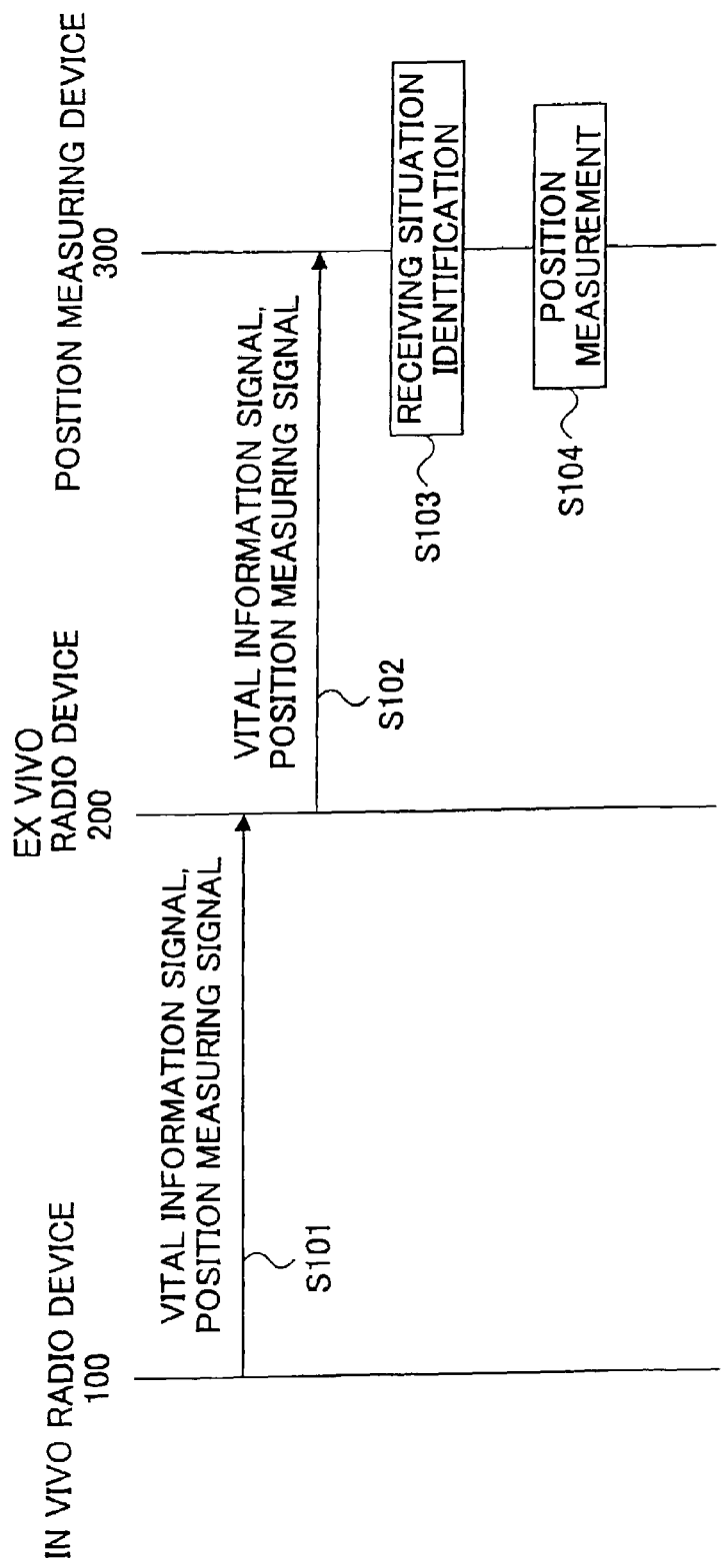
FIG. 8 is a sequence chart illustrating operation of the position measuring system according the first embodiment of the present invention.

FIG. 8 is a sequence chart illustrating the operation of the position measuring system according the Embodiment 1. The in vivo radio device 100 transmits the vital information signal or the position measuring signal to outside the human body at step 101. The ex vivo radio device 200 receives the vital information signal or the position measuring signal and transmits them to the position measuring device 300 at step 102. The position measuring device 300 identifies receiving characteristics of the signals received by the ex vivo radio device 200 at step 103. Based on the receiving characteristics, the position measuring device 300 measures the position of the in vivo radio device 100 at step 104.

Embodiment 2

Figure 9:
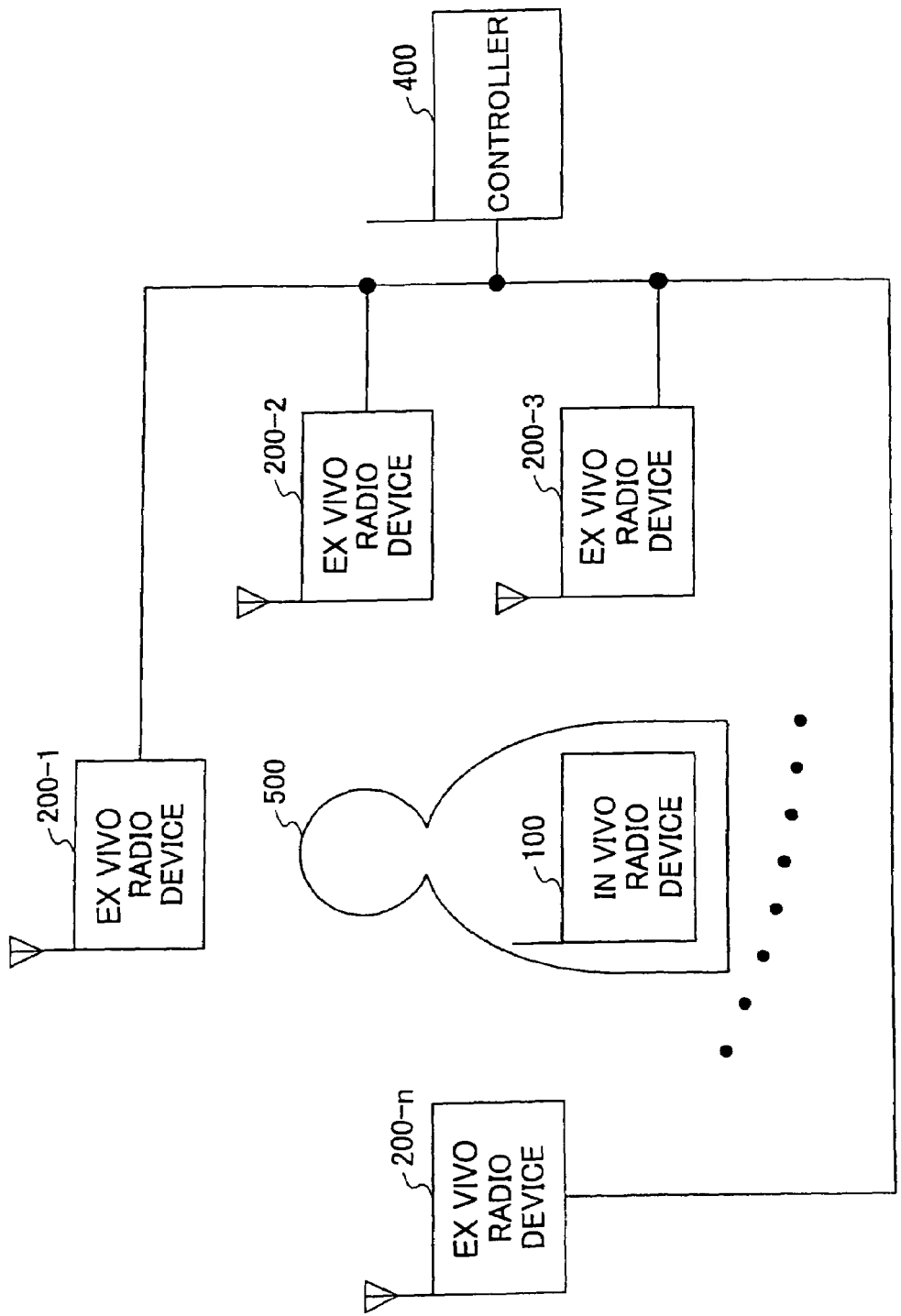
FIG. 9 is a block diagram of a position measuring system according to a second embodiment of the present invention.

FIG. 9 is a block diagram of a position measuring system according to Embodiment 2 of the present invention. The position measuring system shown in FIG. 9 comprises an in vivo radio device 100 administered in a human body, a plurality of ex vivo radio devices 200-1, 200-2, . . . , 200-n (ex vivo radio devices 200) disposed outside of the human body, and a controller 400.

In the position measuring system in

Embodiment 2, the in vivo radio device 100 receives a signal transmitted by each of the ex vivo radio devices 200, and measures the position of the in vivo radio device 100.

FIG. 10 is a block diagram of the in vivo radio device 100 according to Embodiment 2. The in vivo radio device 100 comprises an antenna 101, a transceiving unit 110, a controller 120, a vital information acquisition unit 130 and a position measuring unit 140.

Similar to Embodiment 1, a control signal transmitted by the controller 400 through the ex vivo radio devices 200 is received by the transceiving unit 110 through the antenna 101. The thus received control signal is supplied to the controlling unit 120 to control the operation of the in vivo radio device 100. Based on the control signal, the controlling unit 120 controls the movement of the in vivo radio device 100, provides medication, or conducts in vivo ablation. The controlling unit 120 further controls the vital information acquisition unit 130 based on the received control signal. The vital information acquisition unit 130 includes a built-in camera and a built-in microphone, and takes pictures and collects sounds within the human body and transmits the acquired vital information such as an image signal and a sound signal to the transceiving unit 110. The transceiving unit 110 transmits the vital information signal to the outside of the human body.

The transceiving unit 140 further receives position measuring signals from the ex vivo radio devices 200, and transmits them to the position measuring unit 140. Based on the position measuring signals, the position measuring unit 140 measures the position of the in vivo radio device 100.

Embodiments 2-1, 2-2 and 2-3 are explained below. In Embodiment 2-1, the position measuring unit 140 measures the position of the in vivo radio device 100 based on differences in times when the in vivo radio device 100 receives the signals from the ex vivo radio devices 200. In Embodiment 2-2, the position measuring unit 140 measures a position of the in vivo radio device 100 based on phase differences in signals transmitted from the ex vivo radio devices 200 and received by the in vivo radio device 100. In Embodiment 2-3, the position measuring unit 140 measures the position of the in vivo radio device 100 based on arriving directions of signals transmitted from the ex vivo radio devices 200.

Embodiment 2-1

In this embodiment, the position measuring unit 140 in the in vivo radio device 100 measures the position of the in vivo radio device 100 based on differences in times when the in vivo radio device 100 receives the signals from the ex vivo radio devices 200. More specifically, when the ex vivo radio devices 200 transmit the position measuring signal, they also transmit information on the time of transmitting (hereinafter referred to "transmission time") as a part of the position measuring signal. When the transceiving unit 110 in the in vivo radio device 100 receives the position measuring signals and transmits them to the position measuring unit 140, it also sends information on the time of receiving the position measuring signals (hereinafter referred to "reception time") as a part of the position measuring signals to the position measuring device 140.

The position measuring unit 140 measures or determines the position of the in vivo radio device 100 based on the transmission time and the reception time included in the position measuring signals, and known positions of the ex vivo radio devices 200. More specifically, the procedure is the same as in Embodiment 1-1, and therefore its explanation is omitted.

Embodiment 2-2

In this embodiment, the position measuring unit 140 in the in vivo radio device 100 measures the position of the in vivo radio device 100 based on phase differences in signals transmitted by the ex vivo radio devices 200 and received by the in vivo radio device 100. More specifically, the position measuring unit 140 obtains a receiving phase $\phi_i$ of the position measuring signal transmitted by the ith ex vivo radio device 200-$i$ by Equation 3 above, based on a wavelength $\lambda$ of the position measuring signal, a position $p_0$ of the in vivo radio device 100, and a position $p_i$ of the ith ex vivo radio device 200-$i$. First the position measuring unit 140 obtains the position measuring signal that is a received signal, by Equation 4 above.

Then the position measuring unit 140 calculates a phase difference $\Delta\phi_{ij} = \phi_i - \phi_j$ between a phase $\phi_i$ of the signal transmitted from the ith ex vivo radio device 200-$i$ and a phase $\phi_j$ of the signal transmitted from the jth ex vivo radio device 200-$j$, by obtaining correlation between these signals using Equation 5 above.

On the other hand, a distance difference $r_{ij}$ between the distance $r_i$ between the in vivo radio device 100 and the ith ex vivo radio device 200-$i$ and the distance $r_j$ between the in vivo radio device 100 and the jth ex vivo radio device 200-$j$ can be represented by Equation 6 above. Then the position measuring unit 140 obtains this distance difference $r_{ij}$, based on the phase $\Delta\phi_{ij}$ using Equation 7 above.

The position measuring unit 140 forms three groups, each of which consists of two ex vivo radio devices 200, and substitutes the phase differences corresponding to each group in Equation 7 to obtain each $r_{ij}$. Then the position measuring unit 140 substitutes each of the obtained values $r_{ij}$ in Equation 6 to form three simultaneous equations. Then the position measuring unit 140 obtains the position ($x_0$, $y_0$, $z_0$) of the in vivo radio device 100 by solving the three simultaneous equations.

Embodiment 2-3

In this embodiment, the position measuring unit 140 in the in vivo radio device 100 measures the position of the in vivo radio device 100 based on arriving directions of signals transmitted from the ex vivo radio devices 200. In this case, similar to Embodiment 1-3, the antenna 201 in the in vivo radio devices 100 is an array antenna, especially a linear array antenna for a simple structure. More specifically, the procedure is the same as that in Embodiment 1-3, and therefore its explanation is omitted.

If the moving route of the in vivo radio device 100 is known, the position measuring unit 140 can improve the accuracy of the position of the in vivo radio device 100 by utilizing the route information.

The position measuring unit 140 in the in vivo radio device 100 transmits the thus measured position information via the transceiving unit 110 to the ex vivo radio devices 200. The ex vivo radio devices 200 transmit this position information further to the controller 400. The controller 400 displays the received position information of the in vivo radio device 100 on a monitor to show it to the user.

FIG. 11 is a sequence chart illustrating the operation of the position measuring system according to Embodiment 2. The ex vivo radio devices 200 transmit the position measuring signal into the human body at step 201. The in vivo radio device 100 identifies the receiving characteristics of the position measuring signals at step 201. Based on the receiving characteristics, the in vivo radio device 100 measures its own position at step 203.

The in vivo radio device 100 transmits its measured position information to the ex vivo radio device 200 at step 204. The ex vivo radio device 200 receives the position information and transmits it to the controller 400 at step 205. The controller 400 notifies the user of the received position information at step 206.

According some embodiments of the present invention, the position measuring system can accurately measure the position of the in viva radio device 100, based on the receiving characteristics of the vital information signal or the position measuring signal transmitted from the in vivo radio device 100 and received by the ex vivo radio devices 200, specifically based on any of the receiving time differences, phase differences or arriving directions of signals received by the ex vivo radio devices 200.

According other embodiments of the present invention, the position measuring system can accurately measure the position of the in vivo radio device 100, based on the receiving characteristics of the position measuring signals transmitted from the ex viva radio devices 200 and received by the in viva radio device 100, specifically based on any of the receiving time differences, phase differences or arriving directions of signals transmitted by the ex vivo radio devices 200.

In this manner, the position of an in vivo medical device administered into a human body can be accurately measured according to the embodiments of the present invention.

The present application is based on Japanese Priority Application No. 2003-008739 filed on Jan. 16, 2003 with the Japanese Patent Office, the entire contents of which are hereby incorporated by reference.

Whilst in the present specification and claims the radio devices external to the body are described as "ex vivo radio devices", it will be appreciated that these devices could be in any medium, so that in this context the invention is intended to cover all appropriate ex vivo radio devices.

What is claimed is:

1. A method for measuring a position of an in vivo radio device administered into a living organism, comprising the steps of:
   transmitting a vital information signal or a position measuring signal by the in vivo radio device;
   receiving the vital information signal or the position measuring signal by a plurality of ex vivo radio devices disposed outside of the living organism; and
   measuring with a position measuring unit the position of the in vivo radio device, based on receiving characteristics of the vital information signal or the position measuring signal received by the ex vivo radio devices, wherein the position measuring unit measures the position of the in vivo radio device, based on one of phase differences of the vital information signals or the position measuring signals received by the ex vivo radio devices, and arriving directions of the vital information signals or the position measuring signals received by the ex vivo radio devices.

2. A position measuring system comprising an in vivo radio device administered into a living organism, a plurality of ex vivo radio devices disposed outside of the living organism, and a position measuring device, wherein,
   the in vivo radio device includes a transmitter for transmitting a vital information signal or a position measuring signal;
   each of the ex vivo radio devices includes a receiver for receiving the vital information signal or the position measuring signal; and
   the position measuring device includes a position measuring unit for measuring a position of the in vivo radio device based on receiving characteristics of the vital information signal or the position measuring signal received by the ex vivo radio devices, wherein the position measuring unit measures the position of the in vivo radio device, based on one of phase differences of the vital information signals or the position measuring signals received by the ex vivo radio devices, and arriving directions of the vital information signals or the position measuring signals received by the ex vivo radio devices.

3. A position measuring system comprising an in vivo radio device administered into a living organism, and a plurality of ex vivo radio devices disposed outside of the living organism, wherein, each of the ex vivo radio devices includes a transmitter for transmitting a position measuring signal; and
   the in vivo radio device includes a receiver for receiving the position measuring signals from the ex vivo radio devices, and a position measuring unit for measuring a position of the in vivo radio device based on receiving characteristics of the position measuring signals from the ex vivo radio devices.

4. A position measuring device for measuring a position of an in vivo radio device administered into a living organism, comprising:
   a position measuring unit for measuring the position of the in vivo radio device, based on receiving characteristics of a vital information signal or a position measuring signal transmitted from the in vivo radio device and received by a plurality of ex vivo radio devices, wherein the position measuring unit measures the position of the in vivo radio device, based on one of phase differences of the vital information signals or the position measuring signals received by the ex vivo radio devices, and arriving directions of the vital information signals or the position measuring signals received by the ex vivo radio devices.

5. An in vivo radio device to be administered into a living organism, comprising:
   a receiver for receiving position measuring signals transmitted from a plurality of ex vivo radio devices; and
   a position measuring unit for measuring a position of the in vivo radio device, based on receiving characteristics of the position measuring signals received from the ex vivo radio devices.

6. The in vivo radio device as claimed in claim 5, wherein the position measuring unit measures the position of the in vivo radio device, based on one of differences in receiving times of the position measuring signals received from the ex vivo radio devices, phase differences of the position measuring signals received from the ex vivo radio devices, and arriving directions of the position measuring signals transmitted by the ex vivo radio devices and received by the in vivo radio device.

7. The in vivo radio device as claimed in claim 5, wherein, the position measuring unit notifies the ex vivo radio devices of the measured position.

8. A method for measuring a position of an in vivo radio device administered into a living organism, comprising the steps of:
- transmitting a position measuring signal by a plurality of ex vivo radio devices disposed outside of the living organism;
- receiving the position measuring signals by the in vivo radio device; and
- measuring the position of the in vivo radio device, based on receiving characteristics of the position measuring signals received by the in vivo radio device, wherein the step of measuring the position of the in vivo radio device is based on one of differences in receiving times of the position measuring signals received by the in vivo radio device, phase differences of the position measuring signals received by the in vivo radio device, and arriving directions of the position measuring signals received by the in vivo radio device.

* * * * *